United States Patent
Shaver et al.

(10) Patent No.: US 9,302,974 B1
(45) Date of Patent: Apr. 5, 2016

(54) PROCESS FOR PRODUCING ACETIC ACID

(71) Applicant: Celanese International Corporation, Irving, TX (US)

(72) Inventors: Ronald D. Shaver, Houston, TX (US); Yaw-Haw Liu, Missouri City, TX (US); Mark O. Scates, Houston, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 0 days.

(21) Appl. No.: 14/788,928

(22) Filed: Jul. 1, 2015

(51) Int. Cl.
  *C07C 51/44* (2006.01)
  *C07C 51/09* (2006.01)

(52) U.S. Cl.
  CPC .............. *C07C 51/44* (2013.01); *C07C 51/09* (2013.01)

(58) Field of Classification Search
  CPC ............................. C07C 51/44; C07C 51/09
  USPC ............................................... 562/608
  See application file for complete search history.

(56) References Cited

U.S. PATENT DOCUMENTS

| | | | |
|---|---|---|---|
| 3,769,329 A | 10/1973 | Paulik et ai. | |
| 3,791,935 A | 2/1974 | Eubanks et al. | |
| 4,008,131 A | 2/1977 | Price | |
| 4,615,806 A | 10/1986 | Hilton | |
| 5,001,259 A | 3/1991 | Smith et al. | |
| 5,026,908 A | 6/1991 | Smith et al. | |
| 5,144,068 A | 9/1992 | Smith et al. | |
| 5,416,237 A | 5/1995 | Aubigne et al. | |
| 5,653,853 A | 8/1997 | Kagotani et al. | |
| 5,696,284 A | 12/1997 | Baker et al. | |
| 5,731,252 A | 3/1998 | Warner et al. | |
| 5,877,347 A | 3/1999 | Ditzel et al. | |
| 5,877,348 A | 3/1999 | Ditzel et al. | |
| 5,880,311 A * | 3/1999 | Uemura | B01J 8/007 560/231 |
| 5,883,295 A | 3/1999 | Sunley et al. | |
| 5,932,764 A | 8/1999 | Morris et al. | |
| 5,942,460 A | 8/1999 | Garland et al. | |
| 6,143,930 A | 11/2000 | Singh et al. | |
| 6,225,498 B1 | 5/2001 | Blay et al. | |
| 6,339,171 B1 | 1/2002 | Singh et al. | |
| 6,458,996 B1 | 10/2002 | Muskett | |
| 6,552,221 B1 * | 4/2003 | Hallinan | B01J 19/0006 562/517 |
| 6,657,078 B2 | 12/2003 | Scates et al. | |
| 6,677,480 B2 | 1/2004 | Huckman et al. | |
| 7,005,541 B2 | 2/2006 | Cheung et al. | |
| 7,223,883 B2 | 5/2007 | Picard et al. | |

(Continued)

FOREIGN PATENT DOCUMENTS

| | | |
|---|---|---|
| JP | 4489487 B2 | 6/2010 |
| WO | 2014/115826 A1 | 7/2014 |

OTHER PUBLICATIONS

Zhu, Y. et al. (Apr. 2009). "Techno-economic Analysis for the Thermochemical Conversion of Lignocellulosic Biomass to Ethanol via Acetic Acid Synthesis," prepared for U.S. Department of Energy, PNNL-18483, Pacific Northwest National Laboratory, Richland, WA, 79 pages.

*Primary Examiner* — Jafar Parsa
*Assistant Examiner* — Amy C Bonaparte
(74) *Attorney, Agent, or Firm* — Kilpatrick Townsend & Stockton LLP

(57) ABSTRACT

A process for producing acetic acid is disclosed in which the water concentration is controlled in the side stream between two columns. Controlling the water concentration by a recycle rate of the light liquid phase maintains the hydrogen iodide concentration in the side stream to be up to 50 wppm.

19 Claims, 1 Drawing Sheet

(56) References Cited

U.S. PATENT DOCUMENTS

| | | |
|---|---|---|
| 7,223,886 B2 | 5/2007 | Scates et al. |
| 7,820,855 B2 | 10/2010 | Patt |
| 7,855,306 B2 | 12/2010 | Zinobile et al. |
| 7,884,237 B2 | 2/2011 | Shaver |
| 7,884,241 B2 | 2/2011 | Miura et al. |
| 8,318,977 B2 | 11/2012 | Zinobile et al. |
| 8,697,908 B2 | 4/2014 | Torrence et al. |
| 8,889,904 B2 | 11/2014 | Shaver et al. |
| 9,006,483 B2 | 4/2015 | Shimizu et al. |
| 2002/0151746 A1* | 10/2002 | Scates .................... C07C 51/12 562/519 |
| 2006/0011462 A1 | 1/2006 | Horiguchi et al. |
| 2012/0090981 A1 | 4/2012 | Torrence et al. |
| 2013/0116470 A1 | 5/2013 | Miura et al. |
| 2013/0261334 A1 | 10/2013 | Shimizu et al. |
| 2013/0264186 A1 | 10/2013 | Shimizu et al. |
| 2013/0281735 A1 | 10/2013 | Shimizu et al. |
| 2013/0303800 A1 | 11/2013 | Shimizu |
| 2013/0310603 A1 | 11/2013 | Shimizu et al. |

\* cited by examiner

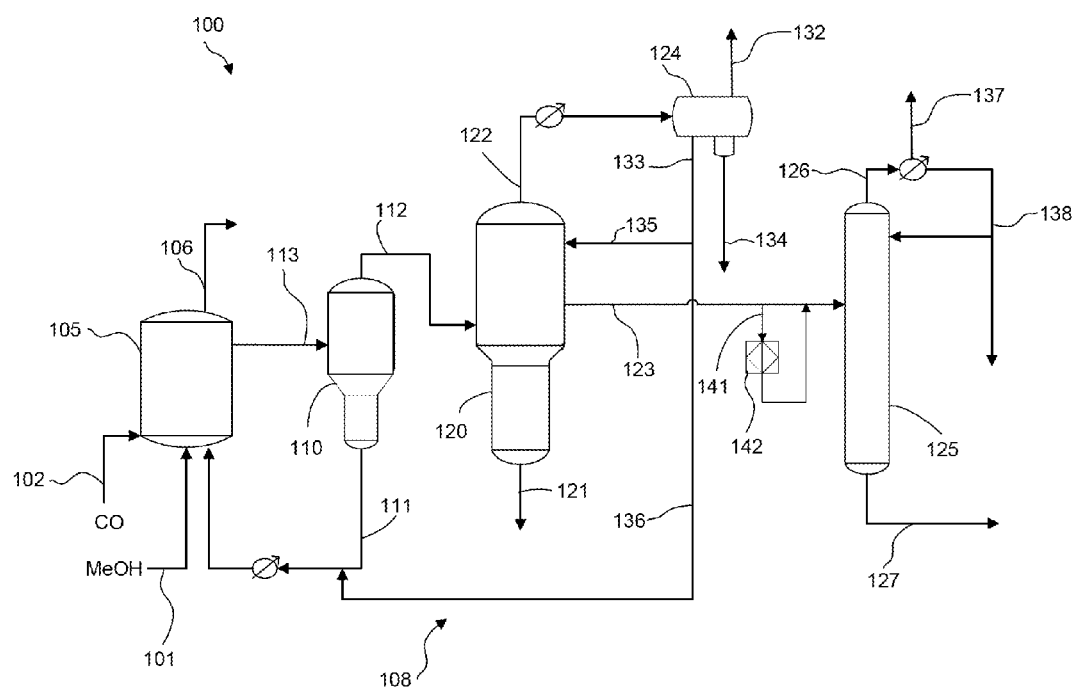

PROCESS FOR PRODUCING ACETIC ACID

FIELD OF THE INVENTION

This invention relates to processes for producing acetic acid and, in particular, to improved processes for controlling the water concentration and the hydrogen iodide concentration fed to the drying column.

BACKGROUND OF THE INVENTION

Among currently employed processes for synthesizing acetic acid, one of the most useful commercially is the catalyzed carbonylation of methanol with carbon monoxide as taught in U.S. Pat. No. 3,769,329, which is incorporated herein by reference in its entirety. The carbonylation catalyst contains a metal catalyst, such as rhodium, which is either dissolved or otherwise dispersed in a liquid reaction medium or supported on an inert solid, along with a halogen-containing catalyst promoter as exemplified by methyl iodide. The reaction is conducted by continuously bubbling carbon monoxide gas through a liquid reaction medium in which the catalyst is dissolved.

Methanol and carbon monoxide are fed to a reactor as feedstocks. A portion of the reaction medium is continuously withdrawn and provided to a flash vessel where the product is flashed and sent as a vapor to a purification train. The purification train includes a light ends column which removes "light" or low boiling components as an overhead and provides a side stream for further purification. The purification train may further include columns to dehydrate the side stream or for removing "heavy" or high boiling components, such as propionic acid, from the side stream. It is desirable in a carbonylation process for making acetic acid to minimize the number of distillation operations to minimize energy usage in the process.

U.S. Pat. No. 5,416,237 discloses a process for the production of acetic acid by carbonylation of methanol in the presence of a rhodium catalyst, methyl iodide, and an iodide salt stabilizer. The improvement according to the '237 patent resides in maintaining a finite concentration of water up to about 10 wt. % and a methyl acetate concentration of at least 2 wt. % in the liquid reaction composition and recovering the acetic acid product by passing the liquid reaction composition through a flash zone to produce a vapor fraction which is passed to a single distillation column from which the acetic acid product is removed. The drawback of eliminating distillation stages is that the level of purity of the product suffers. In particular, the distillation columns tend to remove high boiling iodides as well as aldehyde contamination products. Both of these impurities impact the commercial desirability of the final product.

U.S. Pat. No. 9,006,483 discloses a production process of acetic acid that seeks to inhibit the concentration of hydrogen iodide and provides a liquid-liquid separation of an overhead from a distillation column. Acetic acid is produced by distilling a mixture containing hydrogen iodide, water, acetic acid and methyl acetate in a first distillation column (3) to form an overhead and a side cut stream or bottom stream containing acetic acid, cooling and condensing the overhead in a condenser to form separated upper and lower phases in a decanter (4). According to this process, a zone having a high water concentration is formed in the distillation column above the feed position of the mixture by feeding a mixture having a water concentration of not less than an effective amount to not more than 5% by weight (e.g., 0.5 to 4.5% by weight) and a methyl acetate concentration of 0.5 to 9% by weight (e.g., 0.5 to 8% by weight) as the mixture to the distillation column and distilling the mixture. In the zone having a high water concentration, hydrogen iodide is allowed to react with methyl acetate to produce methyl iodide and acetic acid.

U.S. Pat. No. 7,884,241 discloses a mixture containing hydrogen iodide and water and having a water content of not more than 5% by weight (particularly not more than 3% by weight) in a distillation system is distilled to prevent condensation of hydrogen iodide in the distillation system. The mixture may comprise hydrogen iodide, water, methanol, methyl iodide, acetic acid, and methyl acetate. Even when the mixture contains hydrogen iodide at a concentration of 1 to 3000 ppm on the basis of weight, an acetic acid product having a concentration of hydrogen iodide of not more than 50 ppm can be obtained by withdrawing a fraction containing hydrogen iodide from the top of the column, and withdrawing acetic acid as a side-cut stream or a stream from the bottom of the column. This distillation process can inhibit condensation of hydrogen iodide in the distillation system and corrosion in the distillation system with a large energy penalty. To keep water concentrations low, this process requires a large reflux of 2.35, which is energy intensive.

U.S. Pat. No. 6,657,078 discloses a low energy process for producing acetic acid by the carbonylation of methanol. The process involves a rhodium-catalyzed system operated at less than about 14 wt. % water utilizing up to 2 distillation columns.

U.S. Pat. No. 4,008,131 discloses a method for removal of excess water which tends to build up in recycle streams and reduces the rate of pure acid production during operation of a distillation system for purification of crude acetic acid containing water and methyl iodide. The crude acid is introduced into the upper half of a distillation zone. The methyl iodide, a major proportion of water and an equivalent amount of acid are removed overhead from the zone. A minor proportion of the water containing a small amount of acetic acid is removed as a liquid sidedraw at a point near the top of the distillation zone. A product acid stream essentially dry and substantially free of methyl iodide is removed from the bottom of the distillation zone. The overhead stream can be stored, disposed of or preferably recycled to the acid-producing step. The liquid water sidedraw may either be discarded or subjected to rectification for recovery of acid values.

U.S. Pat. No. 3,791,935 discloses a process by introducing a monocarboxylic acid stream containing water and the halogen contaminant into the upper half of a distillation column, removing an overhead fraction consisting primarily of the water and alkyl halide charged to said column, removing a stream from the middle portion of said column containing a major proportion of hydrogen halide present in said column, and removing a product acid stream from at or near the bottom of said column, the product acid stream being essentially dry and substantially free of the halogen contaminants charged to said column. The method is particularly applicable to the removal of water and iodine-containing compounds from acetic and propionic acids. In the examples, the bottoms product that contains acetic acid is reported to contain from 83 to 132 wppm water and 0.083 wppm to 0.3 wppm hydrogen iodide.

In view of the foregoing, the need exists for an improved acetic acid production process to control recovery of acetic acid.

SUMMARY OF THE INVENTION

In one embodiment the present invention relates to a process for producing acetic acid comprising providing a reaction system comprising a reactor and a flash vessel; forming a reaction medium in the reactor; separating a reaction medium in the flash vessel into a liquid recycle stream and a vapor product stream, distilling at least a portion of the vapor product stream in a first column to obtain a side stream and a low boiling overhead vapor stream comprising more than 5 wt. % water, condensing and biphasically separating at least a portion of the low boiling overhead stream to form a heavy liquid phase and a light liquid phase, controlling a recycle rate of the light liquid phase to the reaction system to maintain a water concentration in the side stream from 1 to 3 wt. % water, e.g., preferably from 1.1 to 2.5 wt. % water, and a hydrogen iodide (HI) concentration up to 50 wppm, e.g., preferably from 0.1 to 50 wppm, and distilling at least a portion of the side stream in a second column to obtain a purified acetic acid product. In one embodiment, the side stream further comprises one or more $C_1$-$C_{14}$ alkyl iodides in an amount from 0.1 to 6 wt. %, and methyl acetate in an amount from 0.1 to 6 wt. %. The light liquid phase optionally comprises from 40 to 80 wt. % water. The reaction medium may comprise from 0.5 to 30 wt. % methyl acetate, from 0.1 to 14 wt. % water, from 200 to 3000 wppm metal catalyst, from 1 to 25 wt. % iodide salt, and from 1 to 25 wt. % methyl iodide. The reaction medium may also comprise acetic acid and methanol. In addition to the recycle of the light liquid phase, a portion of the light liquid phase may also be refluxed to the first column. In one embodiment, the first column is operated with a reflux ratio from 0.05 to 0.4. In some embodiments, another portion of the light liquid phase may be directed to a PRC removal system for removal of acetaldehyde and/or other permanganate reducing compounds. In other embodiments, a portion of the heavy liquid phase may be refluxed to the first column alone or as a mixture with the reflux of the light liquid phase.

Hydrogen iodide concentration in the side stream may be determined by potentiometric titration using lithium acetate as the titrating agent. In response to the measured hydrogen iodide concentration(s), the recycle rate of the light liquid phase may be increased when the measured hydrogen iodide concentration exceeds a determined threshold, e.g., is greater than 50 wppm. In one embodiment, additional steps may be taken to further reduce the iodide concentration of the purified acetic acid product that is withdrawn at or near the bottom of the second column. For example, the present invention may further comprise contacting the purified acetic acid product with a guard bed when the total iodide concentration of the purified acetic acid product is up to 5 wppm, e.g., up to 1 wppm, to remove residual iodide contaminants.

In another embodiment, the present invention relates to a process for producing acetic acid comprising providing a reaction system comprising a reactor and a flash vessel; forming a reaction medium in the reactor; separating the reaction medium in the flash vessel into a liquid recycle stream and a vapor product stream; distilling at least a portion of the vapor product stream in a first column to obtain a side stream and a low boiling overhead vapor stream; condensing and biphasically separating at least a portion of the low boiling overhead stream to form a heavy liquid phase and a light liquid phase; measuring hydrogen iodide concentration in the side stream; controlling a recycle rate of the light liquid phase to the reaction system in response to the measured hydrogen iodide to maintain up to 50 wppm hydrogen iodide in the side stream, e.g., preferably from 0.1 to 50 wppm; and distilling at least a portion of the side stream in a second column to obtain a purified acetic acid product.

In yet another embodiment, the present invention relates to a process for producing acetic acid comprising providing a reaction system comprising a reactor and a flash vessel; forming a reaction medium in the reactor; separating the reaction medium in the flash vessel into a liquid recycle stream and a vapor product stream; distilling at least a portion of the vapor product stream in a first column to obtain a low boiling overhead vapor stream and a side stream comprising water in an amount from 1 to 3 wt. %, one or more $C_1$-$C_{14}$ alkyl iodides in an amount from 0.1 to 6 wt. %, and hydrogen iodide in an amount up to 50 wppm, e.g., from 1 to 50 wppm; distilling at least a portion of the side stream in a second column to obtain a purified acetic acid product; and contacting the purified acetic acid product with a guard bed when total iodide concentration of the purified acetic acid product is up to 5 wppm.

BRIEF DESCRIPTION OF THE DRAWING

The present invention will be better understood in view of the appended non-limiting FIGURE, wherein:

FIG. 1 is a schematic drawing for producing acetic acid in accordance with the present invention.

DETAILED DESCRIPTION OF THE INVENTION

Introduction

Acetic acid recovery processes typically involve distilling a crude acetic acid product in a first column to form a side stream, and distilling the side stream in a second column to form a purified acetic acid product. The side stream comprises acetic acid, water, and various minor impurities, such as, hydrogen iodide. The first column also forms a low boiling overhead vapor stream, which is typically condensed and biphasically separated into a light liquid phase and a heavy liquid phase.

The present invention provides methods for controlling the water concentration and, indirectly, the hydrogen iodide concentration of the side stream. The water concentration of the side stream may be advantageously maintained within the desired range by controlling a recycle rate of the light liquid phase recovered from the first column to the reaction system, which comprises the reactor and flash vessel. In one embodiment, from 0 to 20% of the total light liquid phase condensed from the low boiling overhead stream is recycled and the remainder may be used as a reflux on the first column or fed to a PRC removal system. In some embodiments, the recycle rate of the light liquid phase may be 0% indicating that there is no recycle to the reaction system and the light liquid phase used as a reflux on the first column or fed to a PRC removal system. Because the light liquid phase may be refluxed to the first column, a change in the reflux ratio also affects recycle rate to the reactor, and ultimately the water and hydrogen iodide content of the side stream. Reducing the hydrogen iodide content of the side stream reduces the total iodide content in the second column and ultimately the purified acetic acid product. Having a low total iodide concentration, e.g., up to 5 wppm, e.g., up to 1 wppm, in the purified acetic acid product allows for the efficient removal of any residual iodide contaminants using a guard bed. This greatly improves the quality of the purified acetic acid product.

In one embodiment, the present invention relates to a process for producing acetic acid comprising providing a reaction system comprising a reactor and a flash vessel; forming a reaction medium in the reactor; separating the reaction medium in the flash vessel into a liquid recycle stream and a vapor product stream; distilling at least a portion of the vapor product stream in a first column to obtain a side stream and a low boiling overhead vapor stream comprising more than 5 wt. % water; condensing and biphasically separating at least a portion of the low boiling overhead stream to form a heavy liquid phase and a light liquid phase; controlling a recycle rate of the light liquid phase to the reaction system to maintain a water concentration in the side stream from 1 to 3 wt. % water and hydrogen iodide concentration in the side stream of up to 50 wppm; and distilling at least a portion of the side stream in a second column to obtain a purified acetic acid product.

In another embodiment, the present invention relates to a process for producing acetic acid comprising providing a reaction system comprising a reactor and a flash vessel; forming a reaction medium in the reactor; separating the reaction medium in the flash vessel into a liquid recycle stream and a vapor product stream; distilling at least a portion of the vapor product stream in a first column to obtain a side stream and a low boiling overhead vapor stream; condensing and biphasically separating at least a portion of the low boiling overhead stream to form a heavy liquid phase and a light liquid phase; measuring hydrogen iodide concentration in the side stream; controlling a recycle rate of the light liquid phase to the reaction system in response to the measured hydrogen iodide to maintain up to 50 wppm hydrogen iodide in the side stream, e.g., preferably from 0.1 to 50 wppm; and distilling at least a portion of the side stream in a second column to obtain a purified acetic acid product.

In yet another embodiment, the present invention relates to a process for producing acetic acid comprising providing a reaction system comprising a reactor and a flash vessel; forming a reaction medium in the reactor; separating the reaction medium in the flash vessel into a liquid recycle stream and a vapor product stream; distilling at least a portion of the vapor product stream in a first column to obtain a low boiling overhead vapor stream and a side stream comprising water in an amount from 1 to 3 wt. %, one or more $C_1$-$C_{14}$ alkyl iodides in an amount from 0.1 to 6 wt. %, and hydrogen iodide in an amount up to 50 wppm, e.g., from 1 to 50 wppm; distilling at least a portion of the side stream in a second column to obtain a purified acetic acid product; and contacting the purified acetic acid product with a guard bed when total iodide concentration of the purified acetic acid product is up to 5 wppm.

By controlling the recycle of the light liquid phase, the water concentration in the side stream between two columns may be maintained within certain concentration limits. The side stream may comprise water in an amount from 1 to 3 wt. %, e.g., from 1 to 2.5 wt. % and more preferably from 1.1 to 2.1 wt. %. A water concentration within this range has been discovered to maintain a hydrogen iodide concentration of up to 50 wppm in the side stream, e.g., from 0.1 to 50 wppm hydrogen iodide, or from 5 to 30 wppm hydrogen iodide. Hydrogen iodide is soluble in acetic acid-water mixtures containing water in an amount from 3 to 8 wt. %, and the solubility of hydrogen iodide decreases as the water concentration decreases. This correlation results in making hydrogen iodide more volatile and thus less hydrogen iodide will be collected in the overhead of the column. Although hydrogen iodide may be corrosive under certain circumstances, some amounts of hydrogen iodide under certain conditions may beneficially act as a catalyst, such as a catalyst for forming dimethyl ether as described in U.S. Pat. No. 7,223,883 (describing the benefits of dimethyl ether formation in certain acetic acid separation processes), the entirety of which is incorporated herein by reference.

The control of the recycle rate of the light liquid phase to the reaction system is an improvement over other processes for controlling hydrogen iodide content, such as those described in U.S. Pat. No. 9,006,483, since the present invention advantageously allows for hydrogen iodide control without introducing additional components into the first column and/or maintaining certain concentrations in a vapor product feed that is sent to the first column. In addition, the process described in U.S. Pat. No. 9,006,483 does not involve controlling the light liquid phase recycle to the reaction system, and thus does not independently allow for the control the water and hydrogen iodide concentrations of the side stream.

The major component in the side stream is acetic acid, and the side stream preferably comprises more than 90 wt. % acetic acid, e.g., more than 94 wt. % or more than 96 wt. %. In terms of ranges, the side stream may comprise acetic acid in an amount from 90 to 99 wt. %, e.g., from 91 to 98 wt. %. Such concentrations allow a majority of the acetic acid that is fed to the first column to be withdrawn in the side stream for further purification in the second column. Preferably, acetic acid is not recovered in the low-boiling vapor stream or high boiling residue stream of the first column.

In addition to acetic acid and water, the side stream may also comprise one or more $C_1$-$C_{14}$ alkyl iodides in an amount from 0.1 to 6 wt. %, and in particular methyl iodide. Other alkyl iodides, such as hexyl iodide, may also be formed from carbonyl impurities such as acetaldehyde. More preferably, the side stream comprises one or more $C_1$-$C_{14}$ alkyl iodides in an amount from 0.5 to 3 wt. %. Due to the presence of water, the side stream may also contain methyl acetate in an amount from 0.1 to 6 wt. %, e.g., from 0.5 to 3 wt. %.

Hydrogen iodide concentration of the side stream is determined by potentiometric titration using lithium acetate as the titrating agent. Others have determined hydrogen iodide content indirectly by calculation. U.S. Pub. No. 2013/0310603, for example, indicates that iodide ion concentration may be calculated by subtracting the iodide ion concentration derived from the iodide salt form (including iodides derived from co-catalysts and metal iodide) from the total concentration of iodide ion ($I^-$). Such indirect calculation techniques are typically inaccurate, resulting in a poor indication of actual hydrogen iodide concentration owing largely to the inaccuracies of the underlying ion measurement methods. In addition, this indirect calculation technique fails to account for other iodide forms because metal cations are measured and incorrectly assumed to be completely associated only with iodide anions while, in fact, the metal cations may be associated with other anions, such as acetate and catalyst anions. In contrast, the direct measurement of hydrogen iodide concentration according to the present invention advantageously reflects the actual hydrogen iodide concentration in the system, and can result in accuracy as low as 0.01%.

By detecting the hydrogen iodide concentration of the side stream, the recycle rate of the light liquid phase may be controlled. For example, when the hydrogen iodide concentration exceeds a pre-determined threshold, such as 50 wppm, the recycle rate of the light liquid phase may be increased. Once the hydrogen iodide concentration is below the determined threshold, such as 10 wppm, the recycle rate of the light liquid phase may be decreased. As described herein, the recycle rate of the light liquid phase is the percent being recycled as compared to the total amount of light liquid phase condensed from the first column overhead. The light liquid phase may be recycled to the reaction system.

Reaction Step

An exemplary reaction and acetic acid recovery system 100 is shown in FIG. 1. As shown, methanol-containing feed stream 101 and carbon monoxide-containing feed stream 102 are directed to liquid phase carbonylation reactor 105, in which the carbonylation reaction occurs to form acetic acid.

Methanol-containing feed stream 101 may comprise at least one member selected from the group consisting of methanol, dimethyl ether, and methyl acetate. Methanol-containing feed stream 101 may be derived in part from a fresh feed or may be recycled from the system. At least some of the methanol and/or reactive derivative thereof will be converted to methyl acetate in the liquid medium by esterification reaction with acetic acid.

Typical reaction temperatures for carbonylation will be from 150 to 250° C., with the temperature range of 180 to 225° C. being a preferred range. The carbon monoxide partial pressure in the reactor may vary widely but is typically from 2 to 30 atm, e.g., from 3 to 10 atm. The hydrogen partial pressure in the reactor is typically from 0.05 to 2 atm, e.g., from 0.25 to 1.9 atm. Because of the partial pressure of by-products and the vapor pressure of the contained liquids, the total reactor pressure will range from 15 to 40 atm. The production rate of acetic acid may be from 5 to 50 mol/L·h, e.g., from 10 to 40 mol/L·h, and preferably about 15 to 35 mol/L·h.

Carbonylation reactor 105 is preferably either a stirred vessel or bubble-column type vessel, with or without an agitator, within which the reacting liquid or slurry contents are maintained, preferably automatically, a predetermined level, which preferably remains substantially constant during normal operation. Into carbonylation reactor 105, fresh methanol, carbon monoxide, and sufficient water are continuously introduced as needed to maintain suitable concentrations in the reaction medium.

The metal catalyst may comprise a Group VIII metal. Suitable Group VIII catalysts include rhodium and/or iridium catalysts. When a rhodium catalyst is used, the rhodium catalyst may be added in any suitable form such that rhodium is in the catalyst solution as an equilibrium mixture including [Rh(CO)$_2$I$_2$]-anion, as is well known in the art. Iodide salts optionally maintained in the reaction mixtures of the processes described herein may be in the form of a soluble salt of an alkali metal or alkaline earth metal, quaternary ammonium, phosphonium salt or mixtures thereof. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; 5,144,068 and 7,005,541, which are incorporated herein by reference in their entireties. The carbonylation of methanol utilizing iridium catalyst is well known and is generally described in U.S. Pat. Nos. 5,942,460, 5,932,764, 5,883,295, 5,877,348, 5,877,347 and 5,696,284, which are incorporated herein by reference in their entireties.

The halogen-containing catalyst promoter of the catalyst system consists of a halogen compound comprising an organic halide. Thus, alkyl, aryl, and substituted alkyl or aryl halides can be used. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter will include methyl halide, and more preferably methyl iodide.

The components of the reaction medium are maintained within defined limits to ensure sufficient production of acetic acid. The reaction medium contains a concentration of the metal catalyst, e.g. rhodium catalyst, in an amount from 200 to 3000 wppm, e.g., from 800 to 3000 wppm, or from 900 to 1500 wppm. The concentration of water in the reaction medium is maintained to be less than 14 wt. %, e.g., from 0.1 wt. % to 14 wt. %, from 0.2 wt. % to 10 wt. % or from 0.25 wt. % to 5 wt. %. Preferably, the reaction is conducted under low water conditions and the reaction medium contains 0.1 to 4.1 wt. % water, e.g., from 0.1 to 3.1 wt. % or from 0.5 to 2.8 wt. %. The concentration of methyl iodide in the reaction medium is maintained to be from 1 to 25 wt. %, e.g., from 5 to 20 wt. %, from 4 to 13.9 wt. % or from 4 to 7 wt. %. The concentration of iodide salt, e.g., lithium iodide, in the reaction medium is maintained to be from 1 to 25 wt. %, e.g., from 2 to 20 wt. %, from 3 to 20 wt. %. The concentration of methyl acetate in the reaction medium is maintained to be from 0.5 to 30 wt. %, e.g., from 0.3 to 20 wt. %, from 0.6 to 4.1 wt. %. The following amounts are based on the total weight of the reaction medium. The concentration of acetic acid in the reaction medium is generally more than 30 wt. %, e.g. more than 40 wt. % or more than 50 wt. %.

In some embodiments, the desired reaction rates are obtained even at low water concentrations by maintaining an ester concentration in the reaction medium of the desired carboxylic acid and an alcohol, desirably the alcohol used in the carbonylation, and an additional iodide ion that is over and above the iodide ion that is present as hydrogen iodide. A desired ester is methyl acetate. The additional iodide ion is desirably an iodide salt, with lithium iodide (LiI) being preferred. It has been found that under low water concentrations, methyl acetate and lithium iodide act as rate promoters only when relatively high concentrations of each of these components are present and that the promotion is higher when both of these components are present simultaneously.

The carbonylation reaction of methanol to acetic acid product may be carried out by contacting the methanol feed with gaseous carbon monoxide bubbled through an acetic acid solvent reaction medium containing the rhodium catalyst, methyl iodide (MeI) promoter, methyl acetate (MeAc), and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or other cations such as those based on amine or phosphine compounds (optionally, ternary or quaternary cations), can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being particularly suitable. In the low water carbonylation process, the additional iodide ion over and above the iodide ion present as hydrogen iodide is generally present in the catalyst solution in amounts such that the total iodide ion concentration is from 1 to 25 wt. % and the methyl acetate is generally present in amounts from 0.5 to 30 wt. %, and the methyl iodide is generally present in amounts from 1 to 25 wt. %. The rhodium catalyst is generally present in amounts from 200 to 3000 ppm.

In a typical carbonylation process, carbon monoxide is continuously introduced into the carbonylation reactor, desirably below the agitator, which may be used to stir the contents. The gaseous feed preferably is thoroughly dispersed through the reacting liquid by this stirring means. Gaseous purge stream 106 desirably is vented from the reactor 105 to prevent buildup of gaseous by-products and to maintain a set carbon monoxide partial pressure at a given total reactor pressure. The temperature of the reactor may be controlled and the carbon monoxide feed is introduced at a rate sufficient to maintain the desired total reactor pressure. Stream 113 comprising the liquid reaction medium exits reactor 105.

The acetic acid production system preferably includes separation system 108 employed to recover the acetic acid and recycle metal catalyst, methyl iodide, methyl acetate, and other system components within the process. One or more of the recycle streams may be combined prior to being introduced into the reactor. The separation system also preferably controls water and acetic acid content in the carbonylation reactor, as well as throughout the system, and facilitates permanganate reducing compound ("PRC") removal. PRC's may include acetaldehyde, acetone, methyl ethyl ketone, butyraldehyde, crotonaldehyde, 2-ethyl crotonaldehyde, 2-ethyl butyraldehyde, and the aldol condensation products thereof.

The reaction medium is drawn off from the carbonylation reactor 105 at a rate sufficient to maintain a constant level therein and is provided to flash vessel 110 via stream 113. Reactor 105 and flash vessel 110, along with the associated pumps, vents, pipes, and values, comprise the reaction system. The flash separation may be carried out at a temperature from 80° C. to 280° C., under an absolute pressure from 0.25 to 10 atm, and more preferably from 100° C. to 260° C. and from 0.3 to 10 atm. In flash vessel 110, the reaction medium is separated in a flash separation step to obtain a vapor product stream 112 comprising acetic acid and liquid recycle stream 111 comprising a catalyst-containing solution.

Liquid recycle stream 111 comprises acetic acid, the metal catalyst, corrosion metals, as well as other various compounds. In one embodiment, liquid recycle stream comprises from 60 to 90 wt. % acetic acid, from 0.01 to 0.5 wt. % metal catalyst; from 10 to 2500 wppm corrosion metals (e.g., nickel, iron and chromium); from 5 to 20 wt. % lithium iodide; from 0.5 to 5 wt. % methyl iodide; from 0.1 to 5 wt. % methyl acetate; from 0.1 to 8 wt. % water; up to 1 wt. % acetaldehyde (e.g., from 0.0001 to 1 wt. % acetaldehyde); and up to 0.5 wt. % hydrogen iodide (e.g., from 0.0001 to 0.5 wt. % hydrogen iodide).

The respective flow rates of vapor product stream 112 and liquid recycle stream 111 may vary, and in one exemplary embodiment 15% to 55% of the flow into flash vessel 110 is removed as vapor product stream 112 and 45% to 85% of the flow is removed as liquid recycle stream 111. The catalyst-containing solution may be predominantly acetic acid containing the rhodium and the iodide salt along with lesser quantities of methyl acetate, methyl iodide, and water and is recycled to the reactor, as discussed above. Prior to returning a liquid recycle stream to the reactor, a slip stream may pass through a corrosion metal removal bed, such as an ion exchange bed, to remove any entrained corrosion metals, such as nickel, iron and chromium, as described in U.S. Pat. No. 5,731,252, which is incorporated herein by reference in their entirety. Also, the corrosion metal removal bed may be used to remove nitrogen compounds, such as amines, as described in U.S. Pat. No. 8,697,908, which is incorporated herein by reference in their entirety.

In addition to acetic acid, vapor product stream 112 also comprises methyl iodide, methyl acetate, water, hydrogen iodide, and PRC's, e.g., acetaldehyde and crotonaldehyde. Dissolved gases exiting reactor 105 and entering flash vessel 110 comprise a portion of the carbon monoxide and may also contain gaseous by-products such as methane, hydrogen, and carbon dioxide. Such dissolved gases exit flash vessel 110 as part of the vapor product stream 112. In one embodiment, carbon monoxide in gaseous purge stream 106 may be fed to the base of flash vessel 110 to enhance rhodium stability.

Recovery of Acetic Acid

The distillation and recovery of acetic acid is not particularly limited for the purposes of the present invention. As shown in FIG. 1, vapor product stream 112 is directed to a first column 120, also referred to as a light ends column. In one embodiment, vapor product stream 112 may comprise acetic acid, methyl acetate, water, methyl iodide, and acetaldehyde, along with other impurities such as hydrogen iodide and crotonaldehyde, and byproducts such as propionic acid. Distillation yields a low-boiling overhead vapor stream 122, a purified acetic acid product that preferably is removed via a side stream 123, and a high boiling residue stream 121. A majority of the acetic acid is removed in side stream 123 and preferably little or no acetic acid is recovered from high boiling residue stream 121.

In one embodiment, low-boiling overhead vapor stream 122 comprises more than 5 wt. % water, e.g., more than 10 wt. % water, or more than 25 wt. % water. The amount of water may be up to 80 wt. %. In terms of ranges, water may be from 5 wt. % to 80 wt. %, e.g., from 10 wt. % to 70 wt. % or from 25 wt. % to 60 wt. %. Reducing water concentration to less than 5 wt. % is not advantageous because this results in a large recycle of acetic acid back to the reaction system which then sets up a large recycle through the entire purification system. In addition to water, low-boiling overhead vapor stream 122 may also comprise methyl acetate, methyl iodide, and carbonyl impurities, such as PRC's, which are preferably concentrated in the overhead to be removed from acetic acid in side stream 123.

As shown, low-boiling overhead vapor stream 122 preferably is condensed and directed to an overhead phase separation unit, as shown by overhead decanter 124. Conditions are desirably maintained such that the condensed low-boiling overhead vapor stream 122, once in decanter 124, will biphasically separate into a light liquid phase 133, also referred to as an aqueous phase, and a heavy liquid phase 134, also referred to as an organic phase. An offgas component may be vented via line 132 from decanter 124. Although the specific compositions of light liquid phase 133 may vary widely, some preferred compositions are provided below in Table 1.

TABLE 1

| Exemplary Light Liquid Phase Compositions | | | |
|---|---|---|---|
|  | conc. (Wt. %) | conc. (Wt. %) | conc. (Wt. %) |
| Water | 40-80 | 50-80 | 60-75 |
| Methyl Acetate | 1-50 | 1-25 | 1-10 |
| Acetic Acid | 1-40 | 1-25 | 15-25 |
| PRC's | Up to 5 | Up to 3 | 0.1-0.7 |
| Methyl Iodide | Up to 10 | Up to 5 | 1-5 |
| HI | Up to 1 | Up to 0.5 | 0.001-0.5 |

The concentration of water and hydrogen iodide in side stream 123 is controlled by the recycle rate of light liquid phase 133 to the reaction system via line 136. The reflux ratio (the mass flow rate of the reflux divided by the total mass flow exiting the top of the column 120, including both heavy liquid phase 134, which may or may not be fully recycled, and the light liquid phase 133) to the first column of the light liquid phase 133 via line 135 preferably is from 0.05 to 0.4, e.g., from 0.1 to 0.35 or from 0.15 to 0.3. In one embodiment, to reduce the reflux ratio, the number of theoretical trays above between the side stream and top of first column may be greater than 5, e.g., preferably greater than 10.

In one embodiment, the recycle of light liquid phase in line 136 to the reaction system is up to about 20%, e.g., up to about 10%, of the total light liquid phase 133 condensed from the first column overhead. In terms of ranges, the recycle of light liquid phase in line 136 may be from 0 to 20%, e.g., from 0.5 to 20% or from 1 to 10%, of the total light liquid phase 133 condensed from the column overhead. The remaining portion may be used as a reflux on the light ends column or fed to a PRC removal system. As shown in FIG. 1, recycle in line 136 may be combined with liquid recycle stream 111 and be returned to reactor 105. In one embodiment, recycle in line 136 may be combined with another stream that is being recycled to the reaction system, e.g., reactor 105 or flash vessel 110. When condensed overhead stream 138 from drying column 125 is phased into an aqueous phase and an organic phase, the recycle in line 136 may be preferably combined with the aqueous phase. Alternatively, recycle in line 136 may be combined, or at least partially combined, with the heavy liquid phase 134 and/or the organic phase from the overhead stream 138.

For purposes of the present invention, a flow valve (not shown) and/or flow monitor (not shown) may be used to control the reflux in line 135 and recycle in line 136. In one embodiment, the controls for the reflux in line 135 and recycle in line 136 may be in communication with on-line analyzer 142 that may provide feedback information to control the respective reflux ratio and recycle to reactor. Changing the reflux ratio may impact the amount of water that is recycled to the reactor. In some embodiments, the amount may be changed so that there is no recycle of the light liquid phase 133 to the reactor. Reducing the reflux (and increasing the recycle to the reactor) decreases the side stream water content. Increasing the reflux increases the water concentration in the side stream and decreases the water recycled to the reactor. Increasing the reflux ratio above 0.4 increases the water concentration to greater than 3 wt. % in side stream, which makes separation in the second column difficult for removing water, methyl acetate, and methyl iodide from the acetic acid. As a result, the acetic acid in the second column bottoms stream may contain a total iodide concentration that is too high for efficient handling by guard beds.

Although not shown, a portion (preferably an aliquot portion) of light liquid phase 133 may be separated and directed to PRC removal system to recover methyl iodide and methyl acetate. As shown in Table 1, light liquid phase 133 contains PRC's, and the process may include removing carbonyl impurities, such as acetaldehyde, that compromise the quality of the acetic acid product and may be removed in suitable impurity removal columns and absorbers as described in U.S. Pat. Nos. 6,143,930; 6,339,171; 7,223,883; 7,223,886; 7,855,306; 7,884,237; 8,889,904; and US Pub. Nos. 2006/0011462, which are incorporated herein by reference in their entireties. Carbonyl impurities, such as acetaldehyde, may react with iodide catalyst promoters to form alkyl iodides, e.g., ethyl iodide, propyl iodide, butyl iodide, pentyl iodide, hexyl iodide, etc. Also, because many impurities originate with acetaldehyde, it is desirable to remove carbonyl impurities from the light liquid phase.

Thus, although not shown in FIG. 1, all or a portion of light liquid phase 133 and/or heavy liquid phase 134 may be directed to a PRC removal system as described above. Preferably the portion(s) directed to the PRC removal system as well as the reflux rate of light liquid phase 133 may be controlled so as to provide the desired balance of water and hydrogen iodide in side stream 123 and water recycle to the reactor.

In some embodiments, all or a portion of heavy liquid phase 134, which contains more methyl acetate and methyl iodide than light liquid phase 133, may also be recycled to reactor 105 and/or refluxed to first column 120. Additional carbonyl impurities may be removed from heavy liquid phase 134 using a similar process as described herein for light liquid phase 133.

In one embodiment, hydrogen iodide concentration in side stream 123 may be determined by feeding a sample stream 141 to an on-line analyzer 142. On-line analyzer 142 may provide real-time or near real-time measurements. In one embodiment, any suitable analyzer may be used, such as, but not limited to, chromatography-mass spectrometry, selected ion monitoring, mass spectrometry, infrared spectroscopy, resonant frequency analyzers or ultrasonic concentration analyzers.

Acetic acid removed via side stream 123 preferably is subjected to further purification, such as in a second column 125, also referred to as a drying column, and separates side stream 123 into overhead stream 126 comprised primarily of water and bottoms stream 127 comprised primarily of acetic acid and may be referred to as the acetic acid product stream. Acetic acid may also be recovered as a side stream near the bottom of second column 125. Overhead stream 126 may comprise 50 to 75 wt. % water. Methyl acetate and methyl iodide are also removed from the side stream and concentrated in the overhead stream. Drying column bottoms stream 127 preferably comprises or consists essentially of acetic acid. In preferred embodiments, drying column bottoms stream 127 comprises acetic acid in an amount greater than 90 wt. %, e.g., greater than 95 wt. % or greater than 98 wt. %. Drying column bottoms stream 127 may be further processed, e.g. by passing through an ion exchange resin, prior to being stored or transported for commercial use.

Similarly, overhead stream 126 from second column 125 contains a reaction component, such as methyl iodide, methyl acetate, and water, and it is preferable to retain these reaction components within the process. As shown, overhead stream 126 is condensed by a heat exchanger into stream 138, which is recycled to reactor 105 and/or refluxed second column 125. An offgas component may be vented via line 137 from condensed low-boiling overhead vapor stream 126. Similar to the condensed low-boiling overhead vapor stream from first column 120, condensed overhead stream 138 may also be separated into an aqueous phase and an organic phase, and these phases may be recycled or refluxed as needed to maintain the desired concentrations in the reaction medium.

To recover residue liquids from the vent stream, in particular lines 106, 132, and 137, these lines may be fed to a scrubber that operates with cooled methanol and/or acetic acid to remove methyl acetate and methyl iodide. A suitable scrubber is described in U.S. Pat. No. 8,318,977, which is incorporated herein by reference in its entirety.

The distillation columns of the present invention may be conventional distillation column, e.g., a plate column, a packed column, and others. The material of the distillation column is not limited and may include a glass, a metal, a ceramic, or other suitable material can be used. For a plate column, the theoretical number of plates may depend on the component to be separated, and may include up to 50 plates, e.g., from 5 to 50, or from 7 to 35.

Guard Bed

Carboxylic acid streams, e.g., acetic acid streams, that are contaminated with a halides and/or corrosion metals may be contacted with the inventive ion exchange resin composition under a wide range of operating conditions. Preferably, the ion exchange resin composition is provided in a guard bed. The use of guard beds to purify contaminated carboxylic acid streams is described, for example, in U.S. Pat. Nos. 4,615,806; 5,653,853; 5,731,252; and 6,225,498, which are hereby incorporated by reference in their entireties. Generally, a contaminated liquid carboxylic acid stream is contacted with the inventive ion exchange resin composition, which is preferably disposed in the guard bed. The halide contaminants, e.g., iodide contaminants, react with the metal to form metal iodides. In some embodiments, hydrocarbon moieties, e.g., methyl groups, that may be associated with the iodide may esterify the carboxylic acid. For example, in the case of acetic acid contaminated with methyl iodide, methyl acetate would be produced as a byproduct of the iodide removal. The formation of this esterification product typically does not have a deleterious effect on the treated carboxylic acid stream.

The pressure during the contacting step is limited only by the physical strength of the resin. In one embodiment, the contacting is conducted at pressures ranging from 0.1 MPa to 1 MPa, e.g., from 0.1 MPa to 0.8 MPa or from 0.1 MPa to 0.5 MPa. For convenience, however, both pressure and temperature preferably may be established so that the contaminated carboxylic acid stream is processed as a liquid. Thus, for example, when operating at atmospheric pressure, which is generally preferred based on economic considerations, the temperature may range from 17° C. (the freezing point of acetic acid) to 118° C. (the boiling point of acetic acid). It is within the purview of those skilled in the art to determine analogous ranges for product streams comprising other carboxylic acid compounds. The temperature of the contacting step preferably is kept relatively low to minimize resin degradation. In one embodiment, the contacting is conducted at a temperature ranging from 25° C. to 120° C., e.g., from 25° C. to 100° C. or from 50° C. to 100° C. Some cationic macroreticular resins typically begin degrading (via the mechanism of acid-catalyzed aromatic desulfonation) at temperatures of 150° C. Carboxylic acids having up to 5 carbon atoms, e.g., up to 3 carbon atoms, remain liquid at these temperatures. Thus, the temperature during the contacting should be maintained below the degradation temperature of the resin utilized. In some embodiments, the operating temperature is kept below temperature limit of the resin, consistent with liquid phase operation and the desired kinetics for halide removal.

The configuration of the guard bed within an acetic acid purification train may vary widely. For example, the guard bed may be configured after a drying column for treating the acetic acid product. Additionally or alternatively, the guard bed may be configured after a heavy ends removal column or finishing column. Preferably the guard bed is configured in a position wherein the temperature acetic acid product stream is low, e.g., less than 120° C. or less than 100° C. Aside from the advantages discussed above, lower temperature operation provides for less corrosion as compared to higher temperature operation. Lower temperature operation provides for less formation of corrosion metal contaminants, which, as discussed above, may decrease overall resin life. Also, because lower operating temperatures result in less corrosion, vessels advantageously need not be made from expensive corrosion-resistant metals, and lower grade metals, e.g., standard stainless steel, may be used.

In one embodiment, the flow rate through the guard bed ranges from 0.1 bed volumes per hour ("BV/hr") to 50 BV/hr, e.g., 1 BV/hr to 20 BV/hr or from 6 BV/hr to 10 BV/hr. A bed volume of organic medium is a volume of the medium equal to the volume occupied by the resin bed. A flow rate of 1 BV/hr means that a quantity of organic liquid equal to the volume occupied by the resin bed passes through the resin bed in a one hour time period.

To avoid exhausting the resin with a purified acetic acid product that is high in total iodide concentration, in one embodiment the purified acetic acid product in bottoms stream 127 is contacted with a guard bed when total iodide concentration of the purified acetic acid product is up to 5 wppm, e.g. preferably up to 1 wppm. In one exemplary embodiment, the total iodide concentration of the purified acetic acid product may be from 0.01 wppm to 5 wppm, e.g., from 0.01 wppm to 1 wppm. Concentrations of iodide above 5 wppm may require re-processing the off-spec acetic acid. Total iodide concentration includes iodide from both organic, $C_1$ to $C_{14}$ alkyl iodides, and inorganic sources, such as hydrogen iodide. A purified acetic acid composition is obtained as a result of the guard bed treatment. The purified acetic acid composition, in one embodiment, comprises less than 100 wppb, iodides, e.g., less than 90 wppb, less than 50 wppb, or less than 25 wppb. In one embodiment, the purified acetic acid composition comprises less than 100 wppb corrosion metals, e.g., less than 750 wppb, less than 500 wppb, or less than 250 wppb. In terms of ranges, the purified acetic acid composition may comprise from 0 to 100 wppb iodides, e.g., from 1 to 50 wppb; and/or from 0 to 1000 wppb corrosion metals, e.g., from 1 to 500 wppb. In other embodiments, the guard bed removes at least 25 wt. % of the iodides from the crude acetic acid product, e.g., at least 50 wt. % or at least 75 wt. %. In one embodiment, the guard bed removes at least 25 wt. % of the corrosion metals from the crude acetic acid product, e.g., at least 50 wt. % or at least 75 wt. %.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

EXAMPLES

The present invention will be better understood in view of the following non-limiting examples.

Comparative Example 1

No Light Liquid Phase Recycle

A typical example of the HI concentration in side stream was determined by titrating 0.2 g of side stream sample with 0.01 M lithium acetate solution in 50 ml acetone. A pH electrode was used with Metrohm 716 DMS Titrino to determine the end point at Dynamic Equivalence-point Titration mode. HI concentration in wt. % was calculated based on the consumption of lithium acetate titrating agent as depicted in following equation.

HI wt. %=(ml of LiOAc)(0.01 M)(128 g/mole)×
100/(g sample)(1000 ml/L)

A sample side stream composition having about 1.9 wt. % water was tested using this HI titration method. The HI concentrations varied from 50 wppm to 300 wppm. No portion of the light liquid phase from the overhead light ends is recycled to the reactor. Without light liquid phase recycle, the HI concentrations tend to be higher.

Example 1

Light Liquid Phase Recycle

A portion of light liquid phase from the overhead light ends is recycled to the reactor to reduce the water content in the side stream. The side stream comprises 1.5 wt. % water with less than 25 wppm HI, and the balance comprising acetic acid, methyl acetate and methyl iodide. HI concentrations were too low to measure directly with titration. There are other cations present that makes directly measuring HI difficult. The measure of total inorganic iodide, i.e. total possible maximize HI, is done directly. These other inorganic iodides may include lithium iodide, as well as corrosion metal iodide.

What is claimed is:

1. A process for producing acetic acid comprising:
   providing a reaction system comprising a reactor and a flash vessel;
   forming a reaction medium in the reactor;
   separating the reaction medium in the flash vessel into a liquid recycle stream and a vapor product stream;
   distilling at least a portion of the vapor product stream in a first column to obtain a side stream and a low boiling overhead vapor stream comprising more than 5 wt. % water;
   condensing and biphasically separating at least a portion of the low boiling overhead stream to form a heavy liquid phase and a light liquid phase;
   controlling a recycle rate of the light liquid phase to the reaction system to maintain a water concentration in the side stream from 1 to 3 wt. % water and hydrogen iodide concentration in the side stream of up to 50 wppm; and
   distilling at least a portion of the side stream in a second column to obtain a purified acetic acid product.

2. The process of claim 1, wherein the reaction medium comprises methyl acetate, water, a metal catalyst, an iodide salt and methyl iodide.

3. The process of claim 1, wherein the reaction medium comprises from 0.5 to 30 wt. % methyl acetate, from 0.1 to 14 wt. % water, from 200 to 3000 wppm metal catalyst, from 1 to 25 wt. % iodide salt, and from 1 to 25 wt. % methyl iodide.

4. The process of claim 1, wherein the water concentration is maintained in the side stream from 1.1 to 2.5 wt. %.

5. The process of claim 1, wherein the hydrogen iodide is maintained in the side stream from 0.1 to 50 wppm.

6. The process of claim 1, wherein the side stream further comprises one or more $C_1$-$C_{14}$ alkyl iodides in an amount from 0.1 to 6 wt. %.

7. The process of claim 1, wherein the side stream further comprises methyl acetate in an amount from 0.1 to 6 wt. %.

8. The process of claim 1, wherein the hydrogen iodide concentration in the side stream is determined by potentiometric titration using lithium acetate as the titrating agent.

9. The process of claim 1, wherein the recycle rate is increased when hydrogen iodide concentration exceeds a determined threshold.

10. The process of claim 1, wherein the first column is operated with a reflux ratio from 0.05 to 0.4.

11. The process of claim 1, further comprising refluxing the heavy liquid phase, the light liquid phase, or a mixture thereof to the first column.

12. The process of claim 1, wherein the light liquid phase comprises from 40 to 80 wt. % water.

13. The process of claim 1, further comprising contacting the purified acetic acid product with a guard bed when total iodide concentration of the purified acetic acid product is up to 5 wppm.

14. A process for producing acetic acid comprising:
   providing a reaction system comprising a reactor and a flash vessel;
   forming a reaction medium in the reactor;
   separating the reaction medium in the flash vessel into a liquid recycle stream and a vapor product stream;
   distilling at least a portion of the vapor product stream in a first column to obtain a side stream and a low boiling overhead vapor stream;
   condensing and biphasically separating at least a portion of the low boiling overhead stream to form a heavy liquid phase and a light liquid phase;
   measuring hydrogen iodide concentration in the side stream;
   controlling a recycle rate of the light liquid phase to the reaction system in response to the measured hydrogen iodide to maintain a water concentration in the side stream from 1 to 3 wt % and a hydrogen iodide concentration in the side stream of up to 50 wppm; and
   distilling at least a portion of the side stream in a second column to obtain a purified acetic acid product.

15. The process of claim 14, wherein the hydrogen iodide concentration in the side stream is measured by potentiometric titration using lithium acetate as the titrating agent.

16. The process of claim 14, wherein the first column is operated with a reflux ratio from 0.05 to 0.4.

17. The process of claim 14, wherein the hydrogen iodide is maintained in the side stream from 0.1 to 50 wppm.

18. A process for producing acetic acid comprising:
   providing a reaction system comprising a reactor and a flash vessel;
   forming a reaction medium in the reactor;
   separating the reaction medium in the flash vessel into a liquid recycle stream and a vapor product stream;
   distilling at least a portion of the vapor product stream in a first column to obtain a low boiling overhead vapor stream and a side stream comprising water in an amount from 1 to 3 wt. %, one or more $C_1$-$C_{14}$ alkyl iodides in an amount from 0.1 to 6 wt. %, and hydrogen iodide in an amount up to 50 wppm;
   distilling at least a portion of the side stream in a second column to obtain a purified acetic acid product; and
   contacting the purified acetic acid product with a guard bed when total iodide concentration of the purified acetic acid product is up to 5 wppm.

19. The process of claim 18, wherein the hydrogen iodide is maintained in the side stream from 0.1 to 50 wppm.

* * * * *